(12) United States Patent
Kameoka et al.

(10) Patent No.: US 10,898,572 B2
(45) Date of Patent: Jan. 26, 2021

(54) STABLE PROTEIN-CONTAINING PREPARATION CONTAINING ARGININAMIDE OR ANALOGOUS COMPOUND THEREOF

(71) Applicant: Chugai Seiyaku Kabushiki Kaisha, Tokyo (JP)

(72) Inventors: Daisuke Kameoka, Tokyo (JP); Masaya Yasutake, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 333 days.

(21) Appl. No.: 15/400,355

(22) Filed: Jan. 6, 2017

(65) Prior Publication Data

US 2017/0112930 A1    Apr. 27, 2017

Related U.S. Application Data

(62) Division of application No. 14/232,922, filed as application No. PCT/JP2012/068276 on Jul. 19, 2012, now Pat. No. 9,574,005.

(30) Foreign Application Priority Data

Jul. 19, 2011 (JP) ................. 2011-157654

(51) Int. Cl.

| A61K 39/395 | (2006.01) |
|---|---|
| A61K 47/18 | (2017.01) |
| A61K 9/08 | (2006.01) |
| C07K 16/28 | (2006.01) |
| A61K 9/00 | (2006.01) |

(52) U.S. Cl.
CPC .......... *A61K 39/39591* (2013.01); *A61K 9/08* (2013.01); *A61K 47/18* (2013.01); *A61K 47/183* (2013.01); *C07K 16/2866* (2013.01); *A61K 9/0019* (2013.01); *C07K 2317/94* (2013.01)

(58) Field of Classification Search
None
See application file for complete search history.

(56) References Cited

U.S. PATENT DOCUMENTS

| 8,632,778 | B2 | 1/2014 | Kakuta et al. |
| 9,574,005 | B2 | 2/2017 | Kameoka et al. |
| 2013/0058958 | A1 | 3/2013 | Bowen et al. |
| 2014/0206845 | A1 | 7/2014 | Kameoka et al. |

FOREIGN PATENT DOCUMENTS

| EP | 0 130 619 A2 | 1/1985 |
| EP | 0 156 242 A2 | 10/1985 |
| EP | 0 187 712 A2 | 7/1986 |
| EP | 1 314 437 A | 5/2003 |
| EP | 1 391 209 A1 | 2/2004 |
| EP | 1 475 101 A1 | 11/2004 |
| EP | 2 238 985 A1 | 10/2010 |
| JP | S60-13718 A | 1/1985 |
| JP | S60-193925 A | 10/1985 |
| JP | S61-218528 A | 9/1986 |
| JP | H05-178719 A | 7/1993 |
| JP | 2004-91469 A | 3/2004 |
| JP | 3976257 B2 | 9/2007 |
| JP | 2007-332093 A | 12/2007 |
| JP | 2009-2709 A | 1/2009 |
| JP | 2009-521482 A | 6/2009 |
| JP | 2009-525986 A | 7/2009 |
| JP | 2010-515742 A | 5/2010 |
| JP | 2010-523493 A | 7/2010 |
| JP | 2013-525484 A | 6/2013 |
| WO | WO 97/04801 A1 | 2/1997 |
| WO | WO 02/13860 A1 | 2/2002 |
| WO | WO 02/098445 A1 | 12/2002 |
| WO | WO 03/068260 A1 | 8/2003 |
| WO | WO 2006/065746 A2 | 6/2006 |
| WO | WO 2006/132363 A1 | 12/2006 |
| WO | WO 2007/076062 A2 | 7/2007 |
| WO | WO 2007/092772 A2 | 8/2007 |
| WO | WO 2008/086395 A2 | 7/2008 |
| WO | WO 2008/121615 A2 | 10/2008 |
| WO | WO 2009/084659 A1 | 7/2009 |
| WO | WO-2009104369 A1 | 8/2009 |
| WO | WO 2011/090088 A1 | 7/2011 |
| WO | WO 2011/139718 A1 | 11/2011 |

OTHER PUBLICATIONS

Unverified English language translation of the abstract, claims, and detailed description of Japanese Patent Publication No. 2004-091469 A, published on Mar. 25, 2014, Japanese Patent Office, Patent & Utility Model Gazette DB, Patent Abstract of Japan.
Unverified English language translation of the claims and detailed description of JP 3976257 B2, published on Sep. 12, 2007, Japanese Patent Office, Patent & Utility Model Gazette DB.
Unverified English language translation of the figures of WO 2011/090088, published on Jul. 28, 2011.
Unverified English language translation of WO 2011/090088, published on Jul. 28, 2011.
Daugherty, A.L., and Mrsny, R.J., "Formulation and delivery issues for monoclonal antibody therapeutics," *Advanced Drug Delivery Reviews* 58:686-706, Elsevier Science Publishers B.V., Netherlands (2006).
Hamada, H., and Shiraki, K., "L-Argininamide improves the refolding more effectively that L-arginine," *Journal of Biotechnology* 130:153-160, Elsevier Science Publishers B.V., Netherlands (2007).
Kameoka, et al., *Abstracts of Annual Meeting of Pharmaceutical Society of Japan* 121(4):16(I-072), Japan (2001).
Kameoka, et al., *Journal of Japanese Biochemical Society* 73(8):947(4P-020), Japan (2001).
Kameoka, D., et al., "Effect of Buffer Species on the Unfolding and the Aggregation of Humanized IgG," *J. Biochem.* 142(3):383-391, The Japanese Biochemical Society, Japan (2007).

(Continued)

*Primary Examiner* — Yunsoo Kim
(74) *Attorney, Agent, or Firm* — Nixon & Vanderhye P.C.

(57) ABSTRACT

Addition of argininamide or valinamide to a highly concentrated antibody solution was found to lead to remarkable stabilization, in particular, stabilization against photostress.

24 Claims, 6 Drawing Sheets

Specification includes a Sequence Listing.

(56) References Cited

OTHER PUBLICATIONS

Kameoka, D., et al., "Effect of the Conformational Stability of the CH2 Domain on the Aggregation and Peptide Cleavage of a Humanized IgG," *Appl Biochem Biotechnol* 164:642-654, Springer (2011).

Matsuoka, T., et al., "Amidated Amino Acids Are Prominent Additives for Preventing Heat-Induced Aggregation of Lysozyme," *Journal of Bioscience and Bioengineering* 103(5):440-443, The Society for Biotechnology, Japan (2007).

Shire, S.J., et al., "Challenges in the Development of High Protein Concentration Formulations," *Journal of Pharmaceutical Sciences* 93(6):1390-1402, American Pharmaceutical Assn., United States (2004).

Shire, S.J., "Formulation and manufacturability of biologics," *Current Opinion in Biotechnology* 20:708-714 Elsevier: Current Biology, England (2009).

Wang, W., et al., "Antibody Structure, Instability, and Formulation," *Journal of Pharmaceutical Sciences* 96(1):1-26, Wiley-Liss, Inc. and the American Pharmacists Association, United States (2007).

International Search Report for International Application No. PCT/JP2012/068276, Japanese Patent Office, Japan, dated Sep. 18, 2012.

Matsuoka, T., et al., "Indispensable Structure of Solution Additives to Prevent Inactivation of Lysozyme for Heating and Refolding," *Biotechnol. Prog.* 25:1515-1524, American Institute of Chemical Engineers, United States (2009).

Fursova, K.K., et al., "Refolding of scFv mini-antibodies using size-exclusion chromatography via arginine solution layer," *J Chromatogr. B* 877:2045-2051, Elsevier B.V., Netherlands (2009).

Wang, W., et al., "Protein aggregation—Pathways and influencing factors," *International Journal of Pharmaceutics* 390:89-99, Elsevier B.V., Netherlands (2010).

Unverified English language translation of Japanese Patent Publication No. H05-178179 A, 8 pages.

Unverified English language translation of Foreign Patent document WO 2006/132363 A1, 59 pages.

Kerwin, B. A. and Remmele, Jr., R. L., "Protect from Light: Photodegradation and Protein Biologics," *J Pharm Sci.*, 96(6):1468-1479 (2007).

Qi, P., et al., "Characterization of the Photodegradation of a Human IgG1 Monoclonal Antibody Formulated as a High-Concentration Liquid Dosage Form," *J Pharm Sci.*, 98(9):3117-3130 (2009).

```
SEQUENCE LISTING

<160> NUMBER OF SEQ ID NOS: 2

<210> SEQ ID NO 1
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
```

```
                245                 250                 255
Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
            435                 440

<210> SEQ ID NO 2
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 2

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

-continued

```
            165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

STABLE PROTEIN-CONTAINING PREPARATION CONTAINING ARGININAMIDE OR ANALOGOUS COMPOUND THEREOF

REFERENCE TO SEQUENCE LISTING SUBMITTED ELECTRONICALLY

The content of the electronically submitted sequence listing (Name 21440670002_sequencelisting.txt; Size: 6.06 kilobytes; and Date of Creation: Jan. 3, 2017) filed with the application is incorporated herein by reference in its entirety.

TECHNICAL FIELD

The present invention relates to stable protein-comprising formulations. In particular, it relates to protein-comprising formulations that are stable against photostress.

BACKGROUND ART

In recent years, various antibody formulations have been developed, and are actually in use. Many of these formulations are being used in intravenous injections, while there is an increasing demand in clinical practice for development of antibody-containing formulations as self-injectable formulations for subcutaneous injection. Designing antibody-containing formulations for subcutaneous injection makes it necessary to increase the antibody concentration in the administered solution, since a single dose of antibody are very high (about 100 to 200 mg) and the injection volume for subcutaneous injection is generally limited.

Highly-concentrated antibody-containing solutions tend to form highly viscous solutions by themselves due to intermolecular interactions and macromolecular protein characteristics. Furthermore, degradation phenomenon such as aggregation becomes problematic when proteins are stored as highly-concentrated solutions, and thus, this degradation must be prevented. In particular, highly-concentrated antibody-containing solutions tend to form aggregates during freeze-thawing, or when stored in liquid or frozen conditions for a long time (Non-Patent Documents 1 and 2).

Currently, methods for stabilizing highly-concentrated antibody-containing formulations often use highly-concentrated formulations prepared using so-called lyophilizing concentration techniques, in which highly-concentrated antibody-containing formulations are prepared by lyophilizing an antibody solution with a relatively low concentration and redissolving the lyophilized formulation with a smaller volume of water than the volume before lyophilization (Patent Document 1). In this case, however, the increased viscosity of the redissolved formulations is of concern because a cryoprotectant such as sugar must be added to produce the lyophilized formulations.

In that aspect, this problem can be avoided when a liquid formulation is prepared without lyophilization. However, as described above, highly-concentrated antibody-containing liquid formulations tend to form aggregates. Nonetheless, such formulations are highly demanded because antibody-containing liquid formulations are easier to handle than lyophilized formulations, and can be readily formulated into prefilled syringe formulations.

To date, various assessments have been made with the objective of stabilizing highly-concentrated antibody solution formulations (Non-Patent Documents 1 to 4). Arginine is useful as a stabilizing agent to be used for highly-concentrated antibody solution formulations, and it has been reported that the use of arginine can provide highly-concentrated protein or antibody formulations which are stable, have low viscosity, and maintain low turbidity (Patent Document 4). Stable antibody-containing formulations suitable for subcutaneous administration which are characterized in containing arginine and methionine, and have suppressed deamidation and dimer generation during long-term storage are also known (Patent Document 2). On the other hand, there are not many reports on highly-concentrated antibody solution formulations regarding stability to light, and methionine is given as an example that has a photostabilization effect on low-concentration peptide hormones (Patent Document 3).

While the mechanism of the stabilization effect of arginine is not yet known, arginine is widely known as an additive for improving protein refolding induced by heat stress (original text: refolding additive) at low protein concentrations. Based on this, better additives that improve refolding from among arginine analogs were examined, and as a result, argininamide has been reported to be a more effective additive for improving refolding than arginine (Non-Patent Document 5 and Patent Document 5). Amidated amino acids have inhibitory effects against aggregation induced by heat stress, and in such cases, amino groups and amide groups have been reported to be more effective than guanidinium groups (Non-Patent Document 6). Furthermore, arginine ethyl ester is known to have a stabilization effect against heat stress (Patent Document 6).

PRIOR ART DOCUMENTS

Patent Documents

[Patent Document 1] WO 1997/004801
[Patent Document 2] WO 2009/084659
[Patent Document 3] Japanese Patent Application Kokai Publication No. (JP-A) 2004-091469 (unexamined, published Japanese patent application)
[Patent Document 4] WO 2006/065746
[Patent Document 5] JP-A (Kokai) 2007-332093
[Patent Document 6] Japanese Patent No. 3976257

Non-Patent Documents

[Non-Patent Document 1] Steven J Shire, et al., Challenges in the development of high protein concentration formulations, J Pharm Sci, 2004, 93 (6), 1390-1402
[Non-Patent Document 2] Steven J. Shire, Curr Opin Biotechnol. 2009 December; 20(6):708-14. Epub 2009 Oct. 31.
[Non-Patent Document 3] Wei Wang, et al., Antibody structure, instability, and formulation, J Pharm Sci, 2007, 96 (1), 1-26
[Non-Patent Document 4] Ann L. Daugherty and Randall J. Mrsny, Formulation and delivery issues for monoclonal antibody therapeutics, Adv Drug Del Rev, 2006, 58 (5-6), 686-706
[Non-Patent Document 5] Hiroyuki Hamada and Kentaro Shiraki, L-Argininamide improves the refolding more effectively than L-arginine, J. Biotechnology, 2007, 130, 153-160
[Non-Patent Document 6] Tsuneyoshi Matsuoka, et al., Amidated Amino Acids Are Prominent Additives for Preventing Heat-Induced Aggregation of Lysozyme, J. Biosci Bioeng, 2007, 103(5), 440-443

SUMMARY OF THE INVENTION

Problems to be Solved by the Invention

An objective of the present invention is to provide stable protein-comprising formulations. In particular, an objective is to provide a protein-comprising formulation which is stable against photostress. Furthermore, an objective is to provide stabilizing agents against photostress, methods for suppressing protein aggregation or destabilization caused by photostress, and methods for manufacturing a stabilized protein-comprising formulation.

Means for Solving the Problems

The inventors conducted dedicated research to achieve the above-mentioned objectives. As a result, they discovered that addition of argininamide, compared to methionine, arginine, and such which have been previously reported, to a protein-containing sample can yield better stabilization effects, in particular, stabilization effects against photostress. They found that stable protein-containing formulations are obtained by adding as a stabilization agent, at least one selected from the group consisting of argininamide, arginine ethyl ester, homoarginine, and valinamide, into a protein-containing sample, and thereby completed the present invention.

Specifically, the present invention provides the following:
[1] a stable protein-comprising formulation, which is characterized in that it comprises argininamide or valinamide;
[2] the formulation of [1], wherein the concentration of argininamide or valinamide is 50 mM to 200 mM;
[3] the formulation of [1] or [2], comprising 1 mM to 500 mM histidine buffer and/or citrate buffer and 1 mg/mL to 250 mg/mL protein;
[4] the formulation of [1] or [2], comprising 1 mM to 500 mM histidine buffer and/or citrate buffer, 1 mM to 1500 mM of at least one amino acid, and 1 mg/mL to 250 mg/mL protein;
[5] the formulation of [1] or [2], comprising 1 mM to 50 mM Tris buffer, 1 mM to 1500 mM of at least one amino acid, and 1 mg/mL to 250 mg/mL protein;
[6] the formulation of any one of [1] to [5], which is a solution formulation;
[7] the formulation of any one of [1] to [6], wherein the pH is 5.0 to 7.0;
[8] the formulation of any one of [1] to [7], wherein the protein is an antibody;
[9] a method for suppressing protein aggregation, comprising adding argininamide or valinamide to a protein-containing sample.
[10] a method for suppressing protein destabilization, comprising adding argininamide or valinamide to a protein-containing sample;
[11] the method of [9] or [10], wherein the protein is an antibody;
[12] a protein-containing formulation which is stable against photostress, comprising as a stabilizing agent at least one selected from the group consisting of argininamide, arginine ethyl ester, homoarginine, and valinamide;
[13] the formulation of [12], wherein the stabilizing agent is argininamide.
[14] the formulation of [12], wherein the stabilizing agent is arginine ethyl ester;
[15] the formulation of [12], wherein the stabilizing agent is homoarginine;
[16] the formulation of [12], wherein the stabilizing agent is valinamide;
[17] the formulation of any one of [12] to [16], wherein the concentration of the stabilizing agent is 50 mM to 200 mM;
[18] the formulation of any one of [12] to [17], comprising 1 mM to 500 mM histidine buffer and/or citrate buffer, 1 mM to 1500 mM of at least one amino acid, and 1 mg/mL to 250 mg/mL protein;
[19] the formulation of any one of [12] to [18], which is a solution formulation;
[20] the formulation of any one of [12] to [19], wherein the pH is 5.0 to 7.0;
[21] the formulation of any one of [12] to [20], wherein the protein is an antibody;
[22] an agent for stabilizing a protein against photostress, comprising as an active ingredient at least one selected from the group consisting of argininamide, arginine ethyl ester, homoarginine, and valinamide;
[23] the agent of [22], wherein the protein is a protein contained in a solution;
[24] the agent of [22] or [23], wherein the protein is an antibody;
[25] a method for suppressing protein aggregation caused by photostress, comprising adding to a protein-comprising sample, at least one selected from the group consisting of argininamide, arginine ethyl ester, homoarginine, and valinamide;
[26] a method for suppressing protein destabilization caused by photostress, comprising adding to a protein-comprising sample, at least one selected from the group consisting of argininamide, arginine ethyl ester, homoarginine, and valinamide;
[27] the method of [25] or [26], wherein the protein is an antibody;
[28] use of at least one selected from the group consisting of argininamide, arginine ethyl ester, homoarginine, and valinamide as an agent for stabilizing a protein solution against photostress; and
[29] a method for producing a stabilized protein-comprising formulation, which comprises a step of adding argininamide to a protein-comprising sample.

MODE FOR CARRYING OUT THE INVENTION

Figure 1:
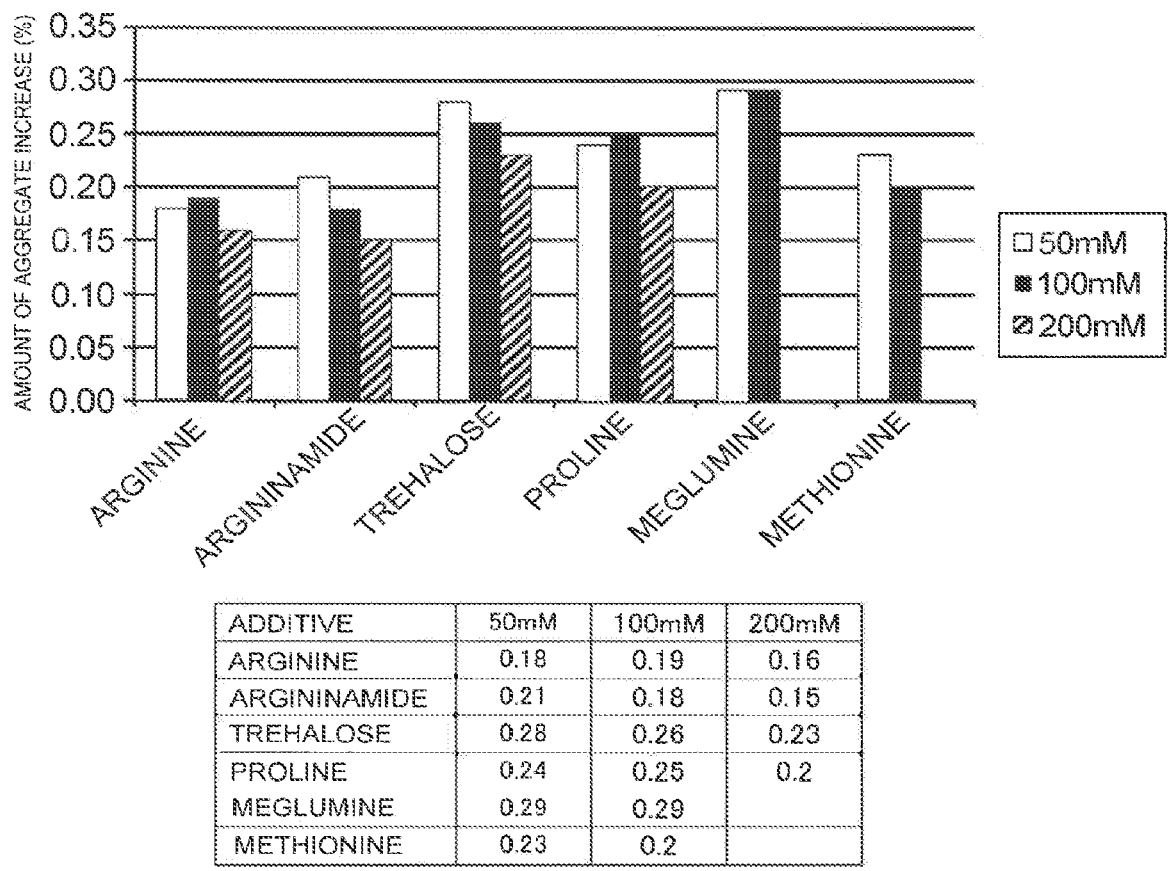
FIG. 1 is a graph that compares the added compounds regarding increase in the amount of aggregates (%) during the two-month storage of Mab1 at 25° C.

To evaluate the stability of a highly-concentrated antibody-containing sample during storage, the present inventors performed size exclusion chromatography to examine the effects of various additives through thermal acceleration study and photostability study. As a result, in a solution produced by dissolving argininamide in a highly-concentrated antibody-containing solution, the amount of aggregate increase was found to be low compared to a solution that does not contain the added argininamide. These results show that argininamide is effective as a stabilizing agent that functions by suppressing aggregate generation. These results of investigation are exemplified in the Examples of the present specification described below as test results using samples comprising two types of humanized anti-IL-6 receptor antibodies or an NR10 humanized antibody.

Specifically, by including argininamide, a stable highly-concentrated antibody-comprising formulation with low antibody aggregate generation can be prepared.

That is, the present invention provides stable protein-comprising formulations which contain argininamide. Furthermore, the present invention relates to methods for suppressing protein aggregation, which include adding argininamide to a protein-comprising sample. The present invention also relates to methods for suppressing destabilization of proteins, which include adding argininamide to a protein-containing sample.

Furthermore, in view of the above-mentioned test results, the present inventors have confirmed the stabilization effect of argininamide and analogous compounds thereof against photostress for protein-containing formulations. As a result, arginine ethyl ester, homoarginine, and valinamide which are argininamide analog compounds were also found to be effective as stabilizing agents, and in particular, argininamide and valinamide were found to be stabilizing agents that improve stability against photostress while maintaining stability during storage.

Accordingly, the present invention provides protein-comprising formulations that are stable against photostress. Here, examples of a stabilizing agent in the protein-comprising formulations that are stable against photostress include not only argininamide, but also arginine ethyl ester, homoarginine, and valinamide. Thus, the present invention provides protein-comprising formulations which are stable against photostress and comprise as a stabilizing agent, at least one selected from the group consisting of argininamide, arginine ethyl ester, homoarginine, and valinamide. Specifically, the present invention relates to formulations comprising argininamide as a stabilizing agent, formulations comprising arginine ethyl ester as a stabilizing agent, formulations comprising homoarginine as a stabilizing agent, and formulations comprising valinamide as a stabilizing agent.

As the argininamide used in the present invention, L-argininamide and salts thereof are preferred. The concentration of argininamide used in the formulations of the present invention is preferably 1 mM to 1500 mM, more preferably 50 mM to 1000 mM, and even more preferably 50 mM to 200 mM. That is, for a concentration between 50 mM and 200 mM, the concentration may be 60 mM, 70 mM, 80 mM, 90 mM, 100 mM, 110 mM, 120 mM, 130 mM, 140 mM, 150 mM, 160 mM, 170 mM, 180 mM, or 190 mM. As the valinamide used in the present invention, L-valinamide and salts thereof are preferred. The concentration of valinamide used in the formulations of the present invention is preferably 1 mM to 1500 mM, more preferably 50 mM to 1000 mM, and even more preferably 50 mM to 200 mM. That is, for a concentration between 50 mM and 200 mM, the concentration may be 60 mM, 70 mM, 80 mM, 90 mM, 100 mM, 110 mM, 120 mM, 130 mM, 140 mM, 150 mM, 160 mM, 170 mM, 180 mM, or 190 mM. Furthermore, the concentration of at least one stabilizing agent selected from the group consisting of argininamide, arginine ethyl ester, homoarginine, and valinamide, which is used in the formulations of the present invention, is preferably 1 mM to 1500 mM, more preferably 50 mM to 1000 mM, and even more preferably 50 mM to 200 mM. That is, for a concentration between 50 mM and 200 mM, the concentration may be 60 mM, 70 mM, 80 mM, 90 mM, 100 mM, 110 mM, 120 mM, 130 mM, 140 mM, 150 mM, 160 mM, 170 mM, 180 mM, or 190 mM.

The protein-comprising formulation in the present invention is a formulation comprising a protein as an active ingredient. The formulation of the present invention preferably includes a glycosylated protein as the protein. Furthermore, in the formulations of the present invention, the protein is preferably an antibody. That is, the present invention relates to formulations that comprise an antibody as an active ingredient and are prepared so that they can be administered to animals including humans. The present invention enables stabilization of a formulation by adding argininamide as a stabilizing agent into a highly-concentrated antibody-containing formulation.

The formulation of the present invention is preferably a formulation in the form of a solution or a liquid. The solution or liquid formulation may contain a buffer. The solution or liquid formulation includes a solution or liquid prior to freeze-drying treatment, and a solution or a liquid obtained after re-dissolution. The formulation of the present invention is preferably a solution or liquid formulation produced without performing a freeze-drying step in the manufacturing process.

Significant changes are not observed for the solution or liquid formulations of the present invention for at least 12 months, preferably two years, and more preferably three years at a refrigeration temperature (2° C. to 8° C.), or for at least six months, preferably one year, and more preferably two years at room temperature (22° C. to 28° C.). The solution or liquid formulations of the present invention are stable for at least six months at 22° C. to 28° C.

In the present invention, being stable means that the formulations of the present invention are formulations that hardly form protein aggregates resulting from long-term storage, freeze-thawing, photostress, or other causes without limitation to those mentioned above, i.e., that they are formulations in which deteriorative reactions such as generation of insoluble and soluble aggregates during storage do not easily occur.

The buffer which may be used in the present invention allows adjustment of pH in a desired range, and is pharmaceutically acceptable. The pH of the formulations of the present invention is preferably 4.5 to 7.0, more preferably 5.0 to 7.0, and even more preferably 5.5 to 6.5. These buffers are known to those skilled in the art, and examples include inorganic salts such as (sodium or potassium) phosphate and sodium hydrogen carbonate; organic acids such as (sodium or potassium) citrate, sodium acetate, and sodium succinate; and acids such as phosphoric acid, carbonic acid, citric acid, succinic acid, malic acid, and gluconic acid. Furthermore, Tris buffer, Good's buffers such as MES and MOPS, histidine (for example, histidine hydrochloride), and glycine may also be used. In the formulations of the present invention, the buffer is preferably a histidine buffer and/or citrate buffer, and a histidine buffer is particularly preferred. The concentration of the buffer is generally 1 mM to 500 mM, preferably 5 mM to 100 mM, and more preferably 15 mM to 25 mM. In addition, when a histidine buffer is used, the buffer contains histidine at a concentration of preferably 10 mM to 30 mM, or more preferably 15 mM to 25 mM.

The formulation of the present invention may contain as a stabilizing agent, not only acidic amino acids such as aspartic acid or glutamic acid, but also amino acids such as methionine, proline, glycine, alanine, phenylalanine, tryptophan, serine, threonine, asparagine, glutamine, arginine, cysteine, histidine, isoleucine, leucine, lysine, tyrosine, and valine. Amino acids of the present invention include free amino acids and salts thereof, such as sodium salts, potassium salts, and hydrochloride salts. Formulations of the present invention preferably contain at least one amino acid from among the amino acids described herein.

The amount of amino acid to be added to the formulations of the present invention is generally 1 mM to 1500 mM, preferably 1 mM to 1000 mM, more preferably 5 mM to 500 mM, and most preferably 10 mM to 300 mM.

As mentioned above, the formulations of the present invention are preferably formulations containing 1 mM to 500 mM histidine buffer and/or citrate buffer, 1 mM to 1500 mM of at least one amino acid, and 1 mg/mL to 250 mg/mL of a protein.

As another embodiment of the formulations of the present invention, formulations containing Tris buffer are also preferred formulations. When Tris buffer is used, the buffer is preferably 1 mM to 50 mM, more preferably 5 mM to 30 mM, and most preferably 10 mM to 20 mM.

The pH or such of the formulations of the present invention can be set to an appropriate range, and the pH is preferably set to 5.0 to 7.0.

In the present invention, the antibody-comprising formulations that are stable against photostress refer to formulations in which aggregates of proteins such as antibodies resulting from photostress are not easily generated; or more specifically, they refer to formulations in which deteriorate reactions including generation of insoluble and soluble aggregates occurring in the solution or during cryopreservation due to photostress do not easily occur.

In the present invention, photostress refers to a condition of receiving light. There are no limitations on the type of light (sun light, laser light, radiation light (electromagnetic wave), etc.), type of light source (sun, artificial light source, etc.), intensity of light, duration of light irradiation, and the duration of receiving light. This is also called photoirradiation stress in the present invention.

The concentration of the antibody contained in a formulation of the present invention is not particularly limited, but the formulation preferably contains a highly-concentrated antibody. That is, the present invention relates to a highly-concentrated antibody-comprising formulation having excellent stability. The antibody concentration is preferably 50 mg/mL or more, more preferably 80 mg/mL or more, even more preferably 100 mg/mL or more, still more preferably 120 mg/mL or more, yet more preferably 0150 mg/mL or more, and still even more preferably 180 mg/mL or more. The upper concentration limit of the antibody contained in a formulation of the present invention is not particularly limited, but it is generally 250 mg/mL.

The antibodies used in the present invention are not particularly limited, as long as they bind to an antigen of interest. The antibodies may be polyclonal or monoclonal antibodies; however, monoclonal antibodies are preferred because they can be stably produced as homogeneous antibodies.

The monoclonal antibodies used in the present invention include not only those derived from animals such as humans, mice, rats, hamsters, rabbits, sheep, camels, and monkeys, but also artificially modified gene recombinant antibodies such as chimeric antibodies, humanized antibodies, and bispecific antibodies. The antibodies of the present invention also include gene recombinant antibodies that result from artificially modifying the antibody constant regions and such to alter the physical properties of the antibody molecule (specifically, alteration of the isoelectric point (pI), improvement of the affinity for Fc receptor, etc.) for the purpose of improving the blood retention and in vivo kinetics.

The immunoglobulin class of the antibodies used in the present invention is not particularly limited; and the class may be any class, including IgG such as IgG1, IgG2, IgG3, and IgG4, IgA, IgD, IgE, and IgM. However, IgG and IgM are preferred.

The above-described antibodies used in the present invention can be prepared by methods known to those skilled in the art.

Basically, monoclonal antibody-producing hybridomas can be prepared by the known methods described below. Specifically, immunization is carried out by a common immunization method using a desired antigen or cells expressing the desired antigen as a sensitizing antigen. The prepared immunocytes are fused with known parental cells by a common cell fusion method. The fused cells are screened for monoclonal antibody-producing cells (hybridomas) by common screening methods. Hybridomas can be generated, for example, according to the method of Milstein et al. (Kohler, G. and Milstein, C., Methods Enzymol. (1981) 73:3-46). When an antigen has low immunogenicity, immunization can be performed using the antigen linked to immunogenic macromolecules such as albumin.

Alternatively, it is possible to use gene recombinant antibodies produced using gene recombination techniques in which antibody genes are cloned from hybridomas and inserted into appropriate vectors, and the resulting vectors are introduced into hosts (see, for example, Carl, A. K. Borrebaeck, James, W. Larrick, Therapeutic Monoclonal Antibodies, Published in the United Kingdom by Macmillan Publishers, 1990). Specifically, cDNAs for antibody variable regions (V regions) are synthesized from the mRNAs of hybridomas using reverse transcriptase. When a DNA encoding an antibody V region of interest is obtained, the DNA is linked to a DNA encoding a desired antibody constant region (C region). The resulting construct is inserted into an expression vector. Alternatively, the antibody V region-encoding DNA may be inserted into an expression vector carrying the DNA of the antibody C region. The construct is inserted into an expression vector so that it is expressed under the control of an expression regulatory region, for example, an enhancer and promoter. Then, host cells are transformed with this expression vector to express the antibody.

In the present invention, artificially modified gene recombinant antibodies such as chimeric and humanized antibodies can be used to reduce heterologous antigenicity against human. Such modified antibodies can be produced using known methods.

A chimeric antibody is an antibody having the heavy-chain and light-chain variable regions of an antibody from a nonhuman mammal such as mouse, and the heavy-chain and light-chain constant regions of a human antibody. The chimeric antibody can be obtained by linking a DNA encoding the variable region of a mouse antibody to a DNA encoding the constant region of a human antibody, inserting the ligate into an expression vector, and then introducing the vector into a host for production.

A humanized antibody is also referred to as reshaped human antibody, and is obtained by substituting the complementarity determining regions (CDR) of a human antibody for the complementarity determining regions of an antibody derived from a nonhuman mammal, for example, mouse. Common gene recombination techniques therefor are also known. Specifically, a DNA sequence is designed to have a mouse antibody CDR linked to a human antibody framework (FR) region, and is synthesized by PCR using several oligonucleotides prepared to have overlapping regions at their ends. The obtained DNA is ligated to a DNA encoding a human antibody constant region and then inserted into an expression vector. The expression vector is introduced into a host to produce the humanized antibody (see, European Patent Application Publication No. EP 239400 and WO 96/02576). The CDR-linked human antibody FR is selected so that the complementarity determining regions form a favorable antigen-binding site. Amino acids in the framework region of the antibody variable region can be substituted as required so that the complementarity determining regions of the reshaped human antibody forms a suitable antigen-binding site (Sato, K. et al., Cancer Res. (1993) 53, 851-856).

Examples of known techniques for substituting amino acids in antibodies to improve antibody activities, physical properties, pharmacokinetics, safety, and such include the techniques described below. The antibodies used in the present invention also include those having such amino acid substitutions.

Techniques are reported for substituting amino acids in the IgG antibody variable regions, and include humanization (Tsurushita N, Hinton P R, Kumar S., Design of humanized antibodies: from anti-Tac to Zenapax, Methods. 2005 May; 36(1):69-83); affinity maturation to enhance the binding activity via amino acid substitution in the complementarity determining region (CDR) (Rajpal A, Beyaz N, Haber L, Cappuccilli G, Yee H, Bhatt R R, Takeuchi T, Lerner R A, Crea R., A general method for greatly improving the affinity of antibodies by using combinatorial libraries, Proc Natl Acad Sci USA. 2005 Jun. 14; 102(24):8466-71); and improvement of physicochemical stability via amino acid substitution in the framework (FR) (Ewert S, Honegger A, Pluckthun A., Stability improvement of antibodies for extracellular and intracellular applications: CDR grafting to stable frameworks and structure-based framework engineering, Methods. 2004 October; 34(2):184-99. Review). Moreover, techniques for enhancing antibody-dependent cell cytotoxicity (ADCC) and complement-dependent cytotoxicity (CDC) are known as techniques of substituting amino acids in an IgG antibody Fc region (Kim S J, Park Y, Hong H J., Antibody engineering for the development of therapeutic antibodies, Mol Cells. 2005 Aug. 31; 20(1): 17-29. Review). Furthermore, in addition to techniques for enhancing the effector functions, there are reports on techniques for improving the antibody half-life in blood by substituting amino acids in Fc (Hinton P R, Xiong J M, Johlfs M G, Tang M T, Keller S, Tsurushita N., An engineered human IgG1 antibody with longer serum half-life, J Immunol. 2006 Jan. 1; 176(1):346-56; Ghetie V, Popov S, Borvak J, Radu C, Matesoi D, Medesan C, Ober R J, Ward E S., Increasing the serum persistence of an IgG fragment by random mutagenesis, Nat Biotechnol. 1997 July; 15(7):637-40). Another known technique includes amino acid substitution technique to control the isoelectric point (pI) of an antibody for the purpose of improving the blood persistence or in vive kinetics, specifically, a technique for modifying amino acid residues exposed on the surface of an antibody to control the pI of the antibody (WO 07/114319). Various techniques to substitute amino acids in the constant regions for the purpose of improving the physical properties of an antibody are also known (WO 09/41613).

Reduction of the dosage of antibody as a pharmaceutical or extension of the interval of antibody administration can be expected by extending the half-life or plasma retention of an antibody. Promising technologies to achieve this include a technique for decreasing the isoelectric point (pI) of the antibody (WO 07/114319). The formulations of the present invention also have a high stabilizing effect for such antibodies with an altered isoelectric point. The isoelectric point-modified antibody refers to a modified antibody whose isoelectric point is lower than that of the original antibody by one or more, preferably two or more, and more preferably three or more. In general, natural (or ordinary) antibodies are assumed to have an isoelectric point within the range of 7.5 to 9.5. The formulations of the present invention have a high stabilizing effect for, in particular, antibodies with a low isoelectric point which hardly exist in nature. The isoelectric point of such antibodies may be 5.0 to 8.0, preferably 5.0 to 7.5, more preferably 5.0 to 7.0, and still more preferably 5.5 to 6.5.

Methods for obtaining human antibodies are also known. For example, desired human antibodies with antigen-binding activity can be obtained by sensitizing human lymphocytes with an antigen of interest or cells expressing an antigen of interest in vitro; and fusing the sensitized lymphocytes with human myeloma cells such as U266 (see Japanese Patent Application Kokoku Publication No. (JP-B) H01-59878 (examined, approved Japanese patent application published for opposition)). Alternatively, desired human antibodies can also be obtained by immunizing transgenic animals having the entire repertoire of human antibody genes with an antigen (see WO 93/12227, WO 92/03918, WO 94/02602, WO 94/25585, WO 96/34096, and WO 96/33735). Furthermore, techniques for obtaining human antibodies by panning with a human antibody library are known. For example, the variable regions of human antibodies can be expressed as single-chain antibodies (scFvs) on the surface of phages using a phage display method, and then phages that bind to the antigen can be selected. The genes of selected phages can be analyzed to determine the DNA sequences that encode the variable regions of human antibodies that bind to the antigen. When the DNA sequences of scFvs that bind to the antigen are identified, appropriate expression vectors carrying these sequences can be constructed to obtain human antibodies. Such methods are already well known. See WO 92/01047, WO 92/20791, WO 93/06213, WO 93/11236, WO 93/19172, WO 95/01438, and WO 95/15388. The antibodies used in the present invention also include such human antibodies.

When the antibody genes are isolated and introduced into appropriate hosts to produce antibodies, hosts and expression vectors can be used in appropriate combinations. When eukaryotic cells are used as a host, animal cells, plant cells, and fungal cells can be used.

The animal cells include: (1) mammalian cells such as CHO, COS, myeloma, baby hamster kidney (BHK), HeLa, and Vero cells; (2) amphibian cells such as *Xenopus* oocytes; and (3) insect cells such as sf9, sf21, and Tn5.

Known plant cells include cells derived from genus *Nicotiana* such as *Nicotiana tabacum*, which can be cultured as a callus.

Known fungal cells include yeasts such as genus *Saccharomyces*, for example *Saccharomyces cerevisiae*, and filamentous fungi such as genus *Aspergillus*, for example *Aspergillus niger*.

When using prokaryotic cells, production systems using bacterial cells can be used. Known bacterial cells include *Escherichia coli* (*E. coli*) and *Bacillus subtilis*. The antibodies can be obtained by introducing the antibody genes of interest into these cells by transformation and then culturing the transformed cells in vitro.

The antibodies used in the present invention include not only whole antibodies but also antibody fragments, minibodies (low molecular weight antibodies), and modified antibodies. Examples of antibody fragments and minibodies include Fab, Fab', F(ab')2, Fv, sFv, dsFv (disulfide-stabilized Fv), and monovalent, bivalent, or higher valency single-chain Fv that result from linking antibody Fvs of the H chain and L chain via a suitable linker such as a peptide linker (scFv, sc(Fv)$_2$, diabodies such as scFv dimer, etc.) (Huston, J. S. et al., Proc. Natl. Acad. Sci. U.S.A. (1988) 85, 5879-5883). Specifically, such antibody fragments are generated by treating antibodies with an enzyme such as papain or pepsin. Alternatively, the gene encoding an antibody fragment is constructed, inserted into an expression vector, and expressed in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Modified antibodies include antibodies linked to polyethylene glycol (PEG) or various molecules such as cytotoxic agents (Farmaco. 1999 Aug. 30; 54(8):497-516; Cancer J. 2008 May-June; 14(3): 154-69). The "antibodies" of the present invention also include such modified antibodies. Such modified antibodies can be prepared by chemically modifying the obtained antibodies. Such methods are already established in this field.

Antibodies used in the present invention include, but are not limited to anti-tissue factor antibodies, anti-IL-6 receptor antibodies, HM1.24 antigen monoclonal antibodies, anti-parathyroid hormone-related peptide antibodies (anti-PTHrP antibodies), anti-ganglioside GM3 antibodies, anti-TPO receptor agonist antibodies, coagulation factor VIII substitute antibodies, anti-IL31 receptor antibodies, anti-HLA antibodies, and anti-CXCR4 antibodies.

Preferred reshaped humanized antibodies used in the present invention include humanized interleukin 6 (IL-6) receptor antibodies (tocilizumab, hPM-1, and MRA) (see WO 92/19759), humanized anti-HM1.24 antigen monoclonal antibodies (see WO 98/14580), humanized anti-parathyroid hormone-related peptide antibodies (anti-PTHrP antibodies) (see WO 98/13388), humanized anti-tissue factor antibodies (see WO 99/51743), and humanized anti-IL-31 receptor antibodies (see WO 2009/072604).

Preferred human IgM antibodies include recombinant human anti-ganglioside GM3 IgM antibodies (see WO 05/05636).

Preferred minibodies include anti-TPO receptor agonist diabodies (see WO 02/33072) and anti-CD47 agonist diabodies (see WO 01/66737).

Furthermore, antibodies with an improved isoelectric point include, for example, Mab1 (H chain/SEQ ID NO: 1; L chain/SEQ ID NO: 2), which is an anti-IL-6 receptor antibody described in WO 2009/041621.

The formulations of the present invention may additionally contain surfactants. Typical examples of the surfactants include nonionic surfactants, for example, sorbitan fatty acid esters such as sorbitan monocaprylate, sorbitan monolaurate, and sorbitan monopalmitate; glycerin fatty acid esters such as glycerol monocaprylate, glycerol monomyristate, and glycerol monostearate; polyglycerol fatty acid esters such as decaglyceryl monostearate, decaglyceryl distearate, and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbitol fatty acid esters such as polyoxyethylene sorbitol tetrastearate and polyoxyethylene sorbitol tetraoleate; polyoxyethylene glycerol fatty acid esters such as polyoxyethylene glyceryl monostearate; polyethyleneglycol fatty acid esters such as polyethyleneglycol distearate; polyoxyethylene alkyl ethers such as polyoxyethylene lauryl ether; polyoxyethylene polyoxyproylene alkyl ethers such as polyoxyethylene polyoxypropylene glycol ether, polyoxyethylene polyoxypropylene propyl ether, and polyoxyethylene polyoxypropylene cetyl ether; polyoxyethylene alkylphenyl ethers such as polyoxyethylenenonylphenyl ether; polyoxyethylene hardened castor oils such as polyoxyethylene castor oil and polyoxyethylene hardened castor oil (polyoxyethylene hydrogenated castor oils); polyoxyethylene beeswax derivatives such as polyoxyethylene sorbitol beeswax; polyoxyethylene lanolin derivatives such as polyoxyethylene lanolin; surfactants with an HLB value of 6 to 18 such as polyoxyethylene fatty acid amides, for example, polyoxyethylene octadecanamide; anionic surfactants, for example, alkyl sulfates with a $C_{10}$-$C_{18}$ alkyl group, such as sodium cetyl sulfate, sodium lauryl sulfate, and sodium oleyl sulfate; polyoxyethylene alkyl ether sulfate in which the number of carbon atoms of the alkyl group is 10 to 18, and the average number of moles per unit of added ethylene oxide is 2 to 4, such as sodium polyoxyethylene lauryl sulfate; alkyl sulfosuccinate salts with a $C_8$-$C_{18}$ alkyl group, such as lauryl sodium sulfosuccinate; naturally occurring surfactants such as lecithin and glycerophospholipids; sphingophospholipids such as sphingomyelin; and sucrose esters of $C_{12}$-$C_{18}$ fatty acids. These surfactants may be added individually to the formulations of the present invention, or two or more of these surfactants may be added in combination.

Preferred surfactants are polyoxyethylene sorbitan fatty acid esters and polyoxyethylene polyoxypropylene alkyl ethers; particularly preferred surfactants are polysorbates (PS) 20, 21, 40, 60, 65, 80, 81, and 85, and Pluronic surfactants; and the most preferred surfactants are polysorbate 20 and 80, and Pluronic F-68 (poloxamer 188 (PX188)).

The amount of surfactant added to the formulations of the present invention is, in general, 0.0001% to 10% (w/v), preferably 0.001% to 5%, and more preferably 0.005% to 3%.

The formulations of the present invention can further contain sugars. The sugars used in the present invention are not particularly limited, and preferred sugars include sucrose, trehalose, mannitol, meglumine, and sorbitol.

The amount of sugar added to the formulations of the present invention is generally 1 mM to 1000 mM, preferably 5 mM to 500 mM, and more preferably 10 mM to 300 mM.

The formulations of the present invention may further contain inorganic salts. The inorganic salts used in the present invention are not particularly limited, and preferred salts include magnesium salts and calcium salts.

If needed, the formulations of the present invention may be appropriately supplemented with ingredients generally added to formulations, such as cryoprotectants, suspending agents, solubilizing agents, isotonizing agents, preservatives, adsorption inhibitors, diluents, excipients, pH adjusting agents, analgesics, sulfur-containing reducing agents, and antioxidants.

Cryoprotectants include, for example, sugars such as trehalose, sucrose, mannitol, meglumine, and sorbitol.

Examples of suspending agents include methyl cellulose, polysorbate 80, hydroxyethyl cellulose, gum arabic, powdered Tragacanth, sodium carboxymethylcellulose, and polyoxyethylene sorbitan monolaurate.

Solubilizing agents include, for example, polyoxyethylene hardened castor oil, polysorbate 80, nicotinamide, polyoxyethylene sorbitan monolaurate, macrogol, and castor oil fatty acid ethyl ester.

Isotonizing agents include, for example, sodium chloride, potassium chloride, and calcium chloride.

Preservatives include, for example, methyl parahydroxybenzoate, ethyl parahydroxybenzoate, ethyl parahydroxybenzoate, sorbic acid, phenol, cresol, and chlorocresol.

Adsorption inhibitors include, for example, human serum albumin, lecithin, dextran, ethylene oxide/propylene oxide copolymer, hydroxypropyl cellulose, methyl cellulose, polyoxyethylene hardened castor oil, and polyethylene glycol.

As diluents, water, ethanol, propylene glycol, ethoxylated isostearyl alcohol, polyoxylated isostearyl alcohol, polyoxyethylene sorbitan fatty acid esters, and such may be used.

As excipients, lactose, fructose, saccharose, glucose, mannitol, sorbitol, sodium chloride, glucose, urea, starch, calcium carbonate, kaolin, crystalline cellulose, silicic acid, silicon dioxide, and such may be used.

Examples of pH adjusting agents include hydrochloric acid, citric acid, succinic acid, acetic acid, boric acid, maleic acid, and sodium hydroxide.

As analgesics, surface anesthetics, local anesthetics, or local paralytic agents are used. Examples of analgesics used in the present invention include benzalkonium chloride, procaine hydrochloride, meprylcaine hydrochloride, lidocaine hydrochloride, lidocaine, chlorobutanol, dibucaine hydrochloride, tetracaine hydrochloride, and ethyl aminobenzoate. A single type of analgesic may be used, or a combination of two or more analgesics may be used.

Sulfur-containing reducing agents include, for example, those containing sulfhydryl groups such as N-acetylcysteine, N-acetylhomocysteine, thioctic acid, thiodiglycol, thioethanol amine, thioglycerol, thiosorbitol, thioglycolic acid and salts thereof, sodium thiosulfate, glutathione, and thioalkanoic acids having one to seven carbon atoms.

Antioxidants include, for example, erythorbic acid, dibutylhydroxytoluene, butylhydroxyanisole, α-tocopherol, tocopherol acetate, L-ascorbic acid and salts thereof, L-ascorbic acid palmitate, L-ascorbic acid stearate, sodium hydrogen sulfite, sodium sulfite, triamyl gallate, propyl gallate, and chelating agents such as disodium ethylenediamine tetraacetate (EDTA), sodium pyrophosphate, and sodium metaphosphate.

Furthermore, the present invention relates to agents for stabilizing proteins under photostress, which comprise as an active ingredient at least one selected from the group consisting of argininamide, arginine ethyl ester, homoarginine, and valinamide. The protein is preferably a protein contained in a solution. The protein in the pharmaceutical agents of the present invention is preferably an antibody.

The present invention also relates to a method for suppressing protein aggregation due to photostress, which includes adding to a protein-containing sample, at least one compound selected from the group consisting of argininamide, arginine ethyl ester, homoarginine, and valinamide.

Furthermore, the present invention relates to a method for suppressing protein destabilization due to photostress, which includes adding to a protein-containing solution, at least one compound selected from the group consisting of argininamide, arginine ethyl ester, homoarginine, and valinamide.

The protein in the methods of the present invention is preferably an antibody. That is, an embodiment of the methods of the present invention is, for example, a method of suppressing photostress-induced antibody aggregation during storage of a formulation in a solution form, by using in the highly-concentrated antibody-containing formulation, at least one compound selected from the group consisting of argininamide, arginine ethyl ester, homoarginine, and valinamide as a stabilizing agent.

The formulations of the present invention may be administered orally or parenterally. In general, the formulations are administered parenterally, specifically via injection, transdermal administration, transmucosal administration, nasal administration, pulmonary administration, or the like.

The dosage forms for oral administration and parenteral administration and methods for manufacturing them are well-known to those skilled in the art, and they can be manufactured according to common methods by, for example, mixing pharmaceutically acceptable carriers and such into a formulation of the present invention.

Injection includes, for example, systemic and local administrations by subcutaneous injection, intravenous injection, intramuscular injection, or such. The injection volume is limited in subcutaneous injection; therefore, a single antibody dose needs to be a large quantity (about 100 to 200 mg). Thus, the formulations of the present invention are particularly suitable for subcutaneous administration (injection).

In terms of pain, it is preferred that the osmotic pressure ratio of the buffering agent is close to isotonic 1.0 in the formulations for subcutaneous administration. Thus, the osmotic pressure of the liquid formulations of the present invention is preferably about 1. Arginine, sugars, and such are added to improve the stability of formulations during storage. However, when the osmotic pressure is greater than the isotonic level, it may cause pain upon subcutaneous administration. Thus, these stabilizers are preferably added while considering the osmotic pressure.

In general, the formulations of the present invention can be provided in containers that have a shape of defined volume such as sealed and sterilized vials, ampules, or syringes made of plastic or glass, or in containers that have a shape of large volume such as bags or bottles. From the viewpoint of convenience, examples of other forms of containers include pre-filled syringes and cartridges for pen-type syringes, but are not limited thereto.

The present invention also provides kits comprising a formulation of the present invention, and kits to be used for the various methods of the present invention. The kits of the present invention comprise a formulation of the present invention. The kits of the present invention can also be suitably packaged with instructions and such describing the method of use.

The present invention also relates to uses of at least one selected from the group consisting of argininamide, arginine ethyl ester, homoarginine, and valinamide as an agent for stabilizing protein solutions against photostress.

Furthermore, the present invention relates to use of argininamide in the manufacture of a stable protein-comprising formulation. The present invention also relates to at least one compound selected from the group consisting of argininamide, arginine ethyl ester, homoarginine, and valinamide in a protein-comprising formulation for use in a method for suppressing protein aggregation in the protein-containing formulation caused by photostress or a method for suppressing protein destabilization due to photostress.

The present invention provides methods for manufacturing formulations of the present invention. That is, the invention also provides a method for manufacturing a stabilized protein-comprising formulation, which includes the step of adding argininamide to a protein-containing sample.

All prior-art documents cited in the specification are incorporated herein by reference.

EXAMPLES

Hereinbelow, the present invention is specifically described with reference to the Examples, but the scope of the present invention is not to be construed as being limited thereto.

[Example 1] Assessment of the Optimal Amount of a Candidate Stabilizing Agent Using Mab1 to be Added Antibody Production Method:

Mab1 (H chain/SEQ ID NO: 1; L chain/SEQ ID NO: 2; an antibody whose isoelectric point has been altered to 5.8), which is an anti-IL-6 receptor antibody described in WO 2009/041621, was expressed by a method known to those skilled in the art using a stably expressing CHO cell line, then purified to high purity by a method known to those skilled in the art including protein A, and used in the stability study described in the Examples below.

Testing Method

The stability of the compound added to the basic formula (Mab1: 180 mg/mL, 20 mM histidine, 100 mM arginine) was evaluated by thermal acceleration test or photoirradiation test using Mab1. Samples were prepared by adding a pre-prepared solution of appropriate composition to a highly concentrated Mab1 stock solution (Mab1: 272 mg/mL, 13.1 mM histidine, 106.0 mg/mL arginine), so that the concentrations of the respective components were adjusted to the concentrations shown in Table 1. Thermal acceleration tests were performed by storing at 25° C. for two months. Photoirradiation tests were performed by irradiating with 1000 lux of light for seven days. The amount of aggregates in each sample after photoirradiation and after two months of storage at 25° C. was calculated by the area percentage method using size exclusion chromatography (SEC). Since an increase of aggregates (%) suggests decreased stability of Mab1, the amount of aggregate increase (%) was used as an indicator for comparing the stability of each formula.

The stabilizing effects of compounds that have a potential stabilizing effect on protein-containing formulations were examined.

Samples were prepared using the aforementioned highly-concentrated Mab1 stock solution, and adjusting the concentrations of each of the components to the concentrations shown in Table 1.

Thermal acceleration tests and photoirradiation tests were each followed by size exclusion chromatography. Each sample was analyzed at its original concentration using a G3000SWXL 7.8 mm I.D.×30 cm column (Tosoh). A 50 mM phosphate buffer (pH7.0) containing 300 mM NaCl was used for the mobile phase, and the analyses were carried out at a flow rate of 0.5 mL/min (detection wavelength: 280 nm). The peak which eluted earlier than the monomer was analyzed as the aggregate, and the peak which eluted later than the monomer was analyzed as low-molecular-weight degradation products; and their respective contents (%) were calculated by the area percentage method.

TABLE 1

| SAMPLE NO. | ANTIBODY mg/mL | HISTIDINE mmol/L | ARGININE mmol/L | ADDITIVE | mmol/L | PX188 mg/mL | pH |
|---|---|---|---|---|---|---|---|
| A1 | 180 | 20 | 100 | ARGININE | 50 | 0.5 | 6.0 |
| A2 | 180 | 20 | 100 | | 100 | 0.5 | 6.0 |
| A3 | 180 | 20 | 100 | | 200 | 0.5 | 6.0 |
| A4 | 180 | 20 | 100 | ARGININAMIDE | 50 | 0.5 | 6.0 |
| A5 | 180 | 20 | 100 | | 100 | 0.5 | 6.0 |
| A6 | 180 | 20 | 100 | | 200 | 0.5 | 6.0 |
| A7 | 180 | 20 | 100 | TREHALOSE | 50 | 0.5 | 6.0 |
| A8 | 180 | 20 | 100 | | 100 | 0.5 | 6.0 |
| A9 | 180 | 20 | 100 | | 200 | 0.6 | 6.0 |
| A10 | 180 | 20 | 100 | PROLINE | 50 | 0.5 | 6.0 |
| A11 | 180 | 20 | 100 | | 100 | 0.5 | 6.0 |
| A12 | 180 | 20 | 100 | | 200 | 0.5 | 6.0 |
| A13 | 180 | 20 | 100 | MEGLUMINE | 50 | 0.5 | 6.0 |
| A14 | 180 | 20 | 100 | | 100 | 0.5 | 6.0 |
| A15 | 180 | 20 | 100 | METHIONINE | 50 | 0.5 | 6.0 |
| A16 | 180 | 20 | 100 | | 100 | 0.5 | 6.0 |

Figure 2:
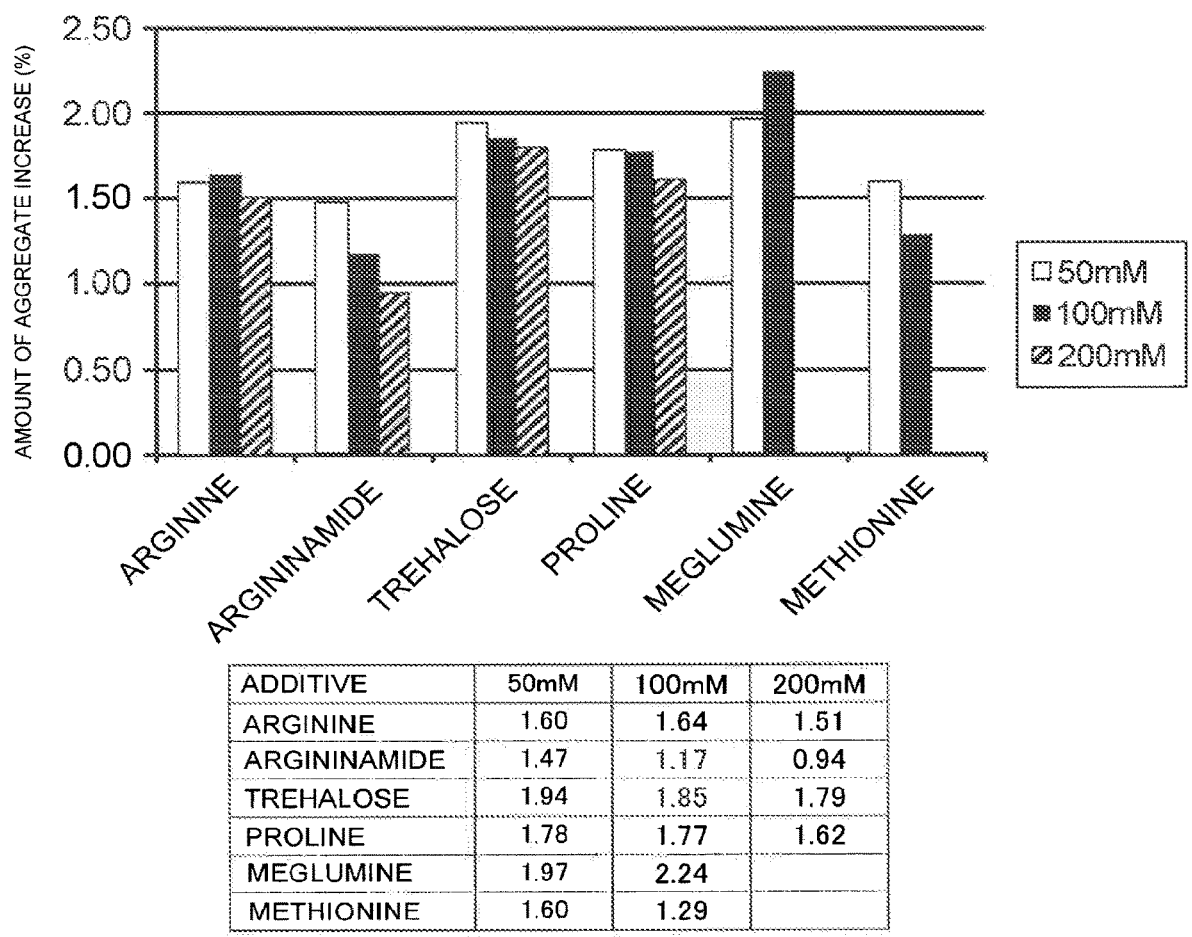
FIG. 2 is a graph that compares the added compounds regarding increase in the amount of aggregates (%) from light irradiation of Mab1.

Results of the amount of aggregate increase (%) for each formula after storage at 25° C. or after photoirradiation are shown in FIGS. 1 and 2, respectively. In the photoirradiation study, the amount of aggregate increased after the study when argininamide was added was clearly reduced compared to that when arginine, which is generally known as a stabilizing agent, was added. The degree of this reduction was concentration-dependent in contrast to the rarely observed concentration-dependent change with arginine. The degree of reduction in the amount of aggregate increase was also found to be the same or higher in comparison to the case with methionine, which is known to have a photostabilizing effect. A same or higher level of reduction in the amount of aggregate increase obtained with arginine was not observed in photoirradiation for other cases where trehalose, proline, and meglumine, which are also known as stabilizing agents, were added. Results with similar trends were observed for the thermal acceleration study, and in the present study, the increase in aggregates was the lowest when 200 mM of argininamide was added.

[Example 2] Assessment of Stabilizing Agent Candidates

In view of the results of Example 1, the stabilization effects of argininamide and analogous compounds thereof on protein-containing formulations were investigated.

Samples were prepared using the aforementioned highly-concentrated Mab1 stock solution by adjusting the concentrations of each of the components to the concentrations shown in Table 2. Thermal acceleration studies and photoirradiation studies were each evaluated by size exclusion chromatography. Each sample was diluted to approximately 1.0 mg/mL using the mobile phase described below, and these were analyzed using a SWXL 6.0 mm I.D.×4 cm (Tosoh) guard column and a G3000SWXL 7.8 mm I.D.×30 cm column (Tosoh). A 50 mM phosphate buffer (pH7.0) containing 300 mM NaCl and 0.05% $NaN_3$ was used for the mobile phase, and the analyses were carried out at a flow rate of 0.5 mL/min (detection wavelength: 280 nm). The peak which eluted earlier than the monomer was analyzed as the aggregate, and the peak which eluted later than the monomer was analyzed as low-molecular-weight degradation products; and their respective contents (%) were calculated by the area percentage method.

TABLE 2

| SAMPLE NO. | ANTI BODY mg/mL | HISTIDINE mmol/L | ARGININE mmol/L | ADDITIVE mmol/L | | PX188 mg/mL | pH |
|---|---|---|---|---|---|---|---|
| B1 | 180 | 20 | 100 | — | 0 | 0.5 | 6.0 |
| B2 | 180 | 20 | 100 | ARGININAMIDE | 150 | 0.5 | 6.0 |
| B3 | 180 | 20 | 100 | ARGININE ETHYL ESTER | 150 | 0.5 | 6.0 |
| B4 | 180 | 20 | 100 | HOMOARGININE | 150 | 0.5 | 6.0 |
| B5 | 180 | 20 | 100 | VALINAMIDE | 150 | 0.5 | 6.0 |
| B6 | 180 | 20 | 100 | ASPARTIC ACID AMIDE | 150 | 0.5 | 6.0 |

Results on the amount of aggregates (%) increased from addition of compounds analogous to argininamide for each formula after photoirradiation or after storage at 25° C. are shown in Tables 3 and 4. Among the argininamide analogous compounds, when arginine ethyl ester was added, the amount of aggregates increased was most reduced, and the next was argininamide. On the other hand, in comparison with the control, arginine ethyl ester remarkably increased the amount of aggregates increased in thermal acceleration studies; and in comparison with the control, argininamide reduced the amount of aggregate increase. In other words, arginine ethyl ester is most suitable when only photostability is considered, but when in consideration of also the results of the thermal acceleration studies, which envision stability during storage, argininamide was found to be a stabilizing agent with improved photostability while retaining stability during storage.

TABLE 3

| ADDITIVE | mmol/L | AMOUNT OF AGGREGATE INCREASE (%) |
|---|---|---|
| — | 0 | 1.22 |
| ARGININAMIDE | 150 | 0.56 |
| ARGININE ETHYL ESTER | 150 | 0.40 |
| HOMOARGININE | 150 | 0.99 |
| VALINAMIDE | 150 | 0.76 |
| ASPARTIC ACID AMIDE | 150 | 1.25 |

TABLE 4

| ADDITIVE | mmol/L | AMOUNT OF AGGREGATE INCREASE (%) |
|---|---|---|
| — | 0 | 0.19 |
| ARGININAMIDE | 150 | 0.12 |
| ARGININE ETHYL ESTER | 150 | 2.97 |
| HOMOARGININE | 150 | 0.14 |
| VALINAMIDE | 150 | 0.16 |
| ASPARTIC ACID AMIDE | 150 | 0.25 |

[Example 3] Assessment of Stabilization Effects Using a Different Formula

Samples were prepared by performing dialysis on the aforementioned highly-concentrated Mab1 stock solution to remove arginine, and then adding a pre-prepared solution of appropriate composition to adjust the concentration of each component to the concentrations shown in Table 5; and the stabilization effects of formulations in a formula different from those of Example 2 were examined. Thermal acceleration studies were performed by storage at 25° C. for one, two, or three months, and storage at 40° C. for two or four weeks; and photoirradiation studies were performed in a similar manner as in Example 1. After the respective studies, each sample was diluted to approximately 1.0 mg/mL using the mobile phase used in Example 1, then size exclusion chromatography was performed under similar conditions to those in Example 1, and the respective contents (%) were calculated by the area percentage method.

TABLE 5

| SAMPLE NO. | ANTIBODY mg/mL | HISTIDINE mmol/L | SODIUM CHLORIDE mmol/L | ADDITIVE | mmol/L | PX188 mg/mL | pH |
|---|---|---|---|---|---|---|---|
| C1 | 120 | 20 | 50 | — | 0 | 0.5 | 6.0 |
| C2 | 120 | 20 | 50 | ARGININE | 150 | 0.5 | 6.0 |
| C3 | 120 | 20 | 50 | ARGININAMIDE | 150 | 0.5 | 6.0 |
| C4 | 120 | 20 | 50 | ARGININE ETHYL ESTER | 150 | 0.5 | 6.0 |
| C5 | 120 | 20 | 50 | HOMOARGININE | 150 | 0.5 | 6.0 |
| C6 | 120 | 20 | 50 | VALINAMIDE | 150 | 0.5 | 6.0 |

Figure 3:
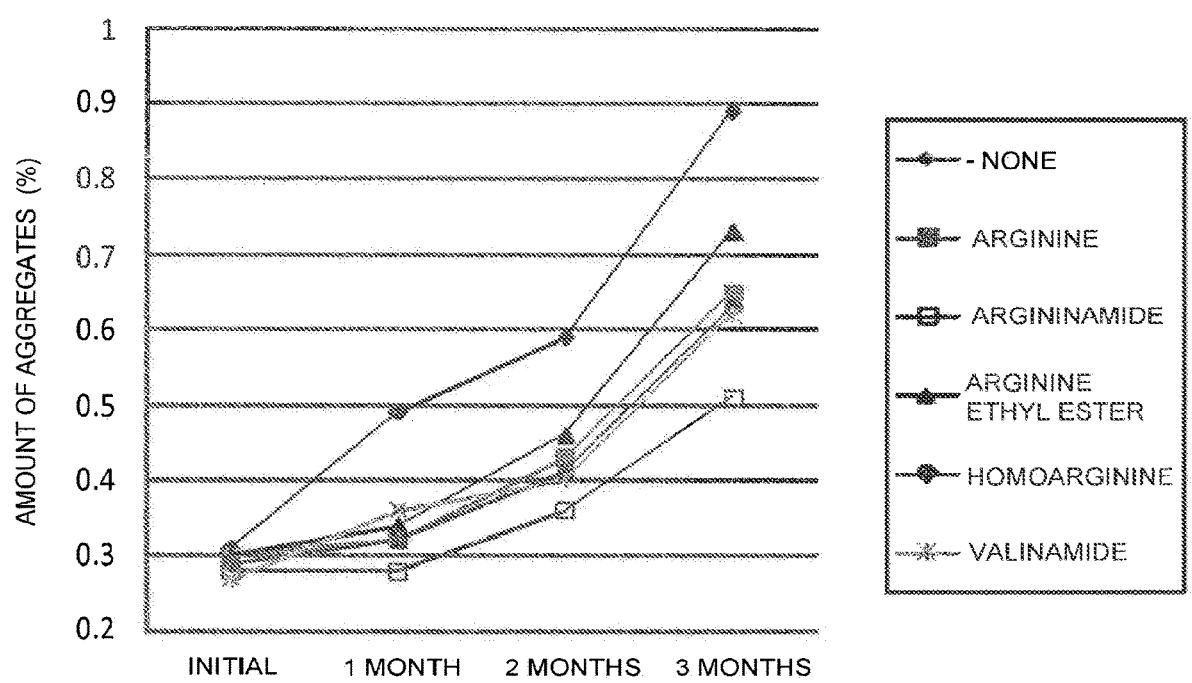
FIG. 3 is a graph showing the changes over time of the amount of aggregates for each of the added compounds when Mab1 was stored at 25° C. for one, two, or three months.
Figure 4:
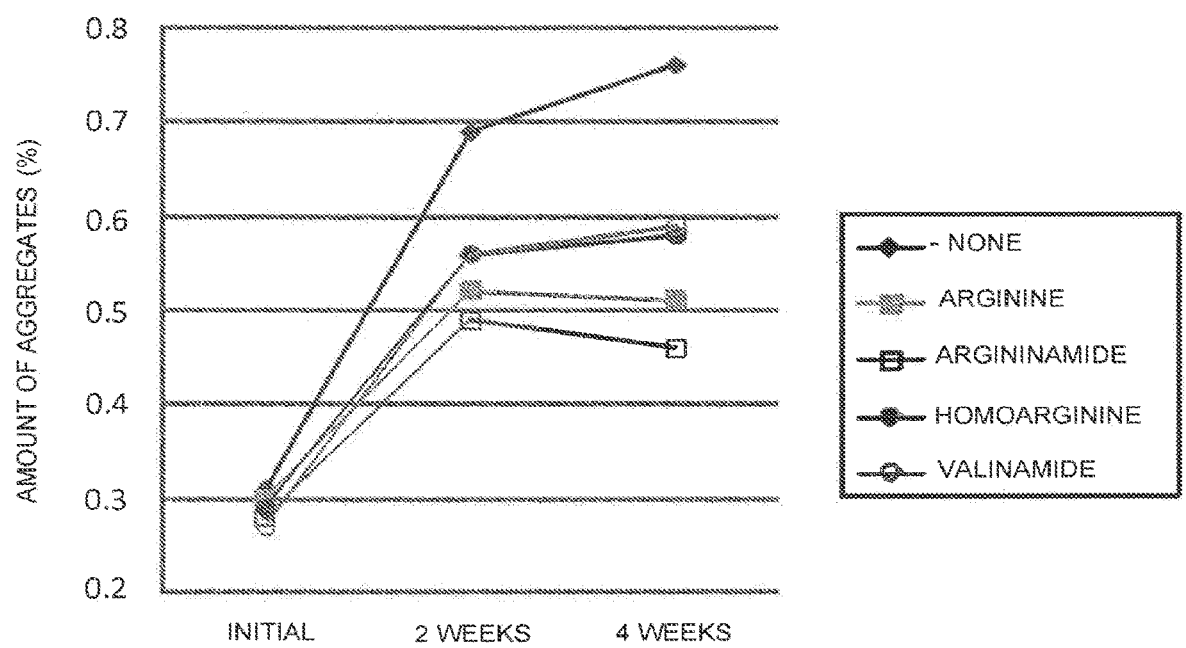
FIG. 4 is a graph showing the changes over time of the amount of aggregates for each of the added compounds when Mab1 was stored at 40° C. for two or four weeks.

Results of the new formula regarding the amount of aggregates (%) increased after two months of storage at 25° C. and after photoirradiation are shown in Tables 6 and 7, respectively. Furthermore, results showing the change over time at 25° C. storage are shown in FIG. 3, and results showing the change over time at 40° C. storage are shown in FIG. 4 and Table 8. Since the amount of aggregates could not be measured for storage at 40° C. due to a gelation phenomenon of the samples, FIG. 4 shows a graph without the data for arginine ethyl ester. In the thermal acceleration study at 25° C., all additive formulas showed a reduced amount of aggregate increase compared to the additive-free formula, but among them, the amount of aggregate increase was lowest when argininamide was added. In the thermal acceleration study at 40° C., all formulas other than the formula containing arginine ethyl ester showed a lower amount of aggregate increase compared to the additive-free formula. In the thermal acceleration studies at both 25° C. and 40° C., an increase in the amount of aggregate increase was observed over time, but the amount of increase was lowest with argininamide. Similarly, in photoirradiation studies, the amount of aggregate increase was low in all formulas containing additives compared to that of the additive-free formula. In the photoirradiation study, the formula showing the lowest amount of aggregate increase was the formula with the addition of arginine ethyl ester; and the formula with the addition of argininamide showed the next lowest amount of aggregate increase.

TABLE 6

| ADDITIVE | mmol/L | AMOUNT OF AGGREGATE INCREASE (%) |
|---|---|---|
| — | 0 | 0.28 |
| ARGININE | 150 | 0.13 |
| ARGININAMIDE | 150 | 0.08 |
| ARGININE ETHYL ESTER | 150 | 0.16 |
| HOMOARGININE | 150 | 0.12 |
| VALINAMIDE | 150 | 0.13 |

TABLE 7

| ADDITIVE | mmol/L | AMOUNT OF AGGREGATE INCREASE (%) |
|---|---|---|
| — | 0 | 2.03 |
| ARGININE | 150 | 1.82 |
| ARGININAMIDE | 150 | 1.07 |
| ARGININE ETHYL ESTER | 150 | 0.90 |
| HOMOARGININE | 150 | 1.75 |
| VALINAMIDE | 150 | 1.48 |

TABLE 8

| ADDITIVE | mmol/L | INITIAL | 2 WEEKS | 4 WEEKS |
|---|---|---|---|---|
| — | 0 | 0.31 | 0.69 | 0.76 |
| ARGININE | 150 | 0.39 | 0.52 | 0.51 |
| ARGININAMIDE | 150 | 0.28 | 0.49 | 0.46 |
| ARGININE ETHYL ESTER | 150 | 0.30 | N.T. | N.T. |
| HOMOARGININE | 150 | 0.29 | 0.56 | 0.58 |
| VALINAMIDE | 150 | 0.27 | 0.56 | 0.59 |

[Example 4] Assessment of Stabilization Effects of Additives Using Mab2

Mab2 which is an NR10 humanized antibody that belongs to the antibody class of IgG2 and whose pI value has been lowered to 5.6 by amino acid sequence alteration (completely humanized NS22 antibody produced by the method described in Example 12 of WO2009/072604) was used for the stability studies in the Example described below.

Testing Method:

Using Mab2, the stability of the compounds added to the basic formula (80 mg/mL Mab2, 20 mM Tris, 50 mM arginine) was evaluated by thermal acceleration test and photoirradiation test. Samples were prepared by adding a pre-prepared solution of appropriate composition to a highly-concentrated Mab2 stock solution (91 mg/mL Mab2, 20 mM Tris, 55.8 mM arginine, pH7.0) to adjust the concentrations of each of the components to the concentrations shown in Table 9. Thermal acceleration studies and photoirradiation studies were carried out under conditions similar to those of Example 3. After the respective studies, size exclusion chromatography was performed under conditions similar to those of Example 3, and the respective contents (%) were calculated by the area percentage method.

TABLE 9

| SAMPLE NO. | ANTIBODY mg/mL | TRIS mmol/L | ARGININE mmol/L | ADDITIVE | mmol/L | PX188 mg/mL | pH |
|---|---|---|---|---|---|---|---|
| D1 | 80 | 20 | 50 | — | | 0 | 0.5 | 7.0 |
| D2 | 80 | 20 | 50 | ARGININAMIDE | 150 | 0.5 | 7.0 |
| D3 | 80 | 20 | 50 | ARGININE ETHYL ESTER | 150 | 0.5 | 7.0 |
| D4 | 80 | 20 | 50 | HOMOARGININE | 150 | 0.5 | 7.0 |
| D5 | 80 | 20 | 50 | VALINAMIDE | 150 | 0.5 | 7.0 |

Figure 5:
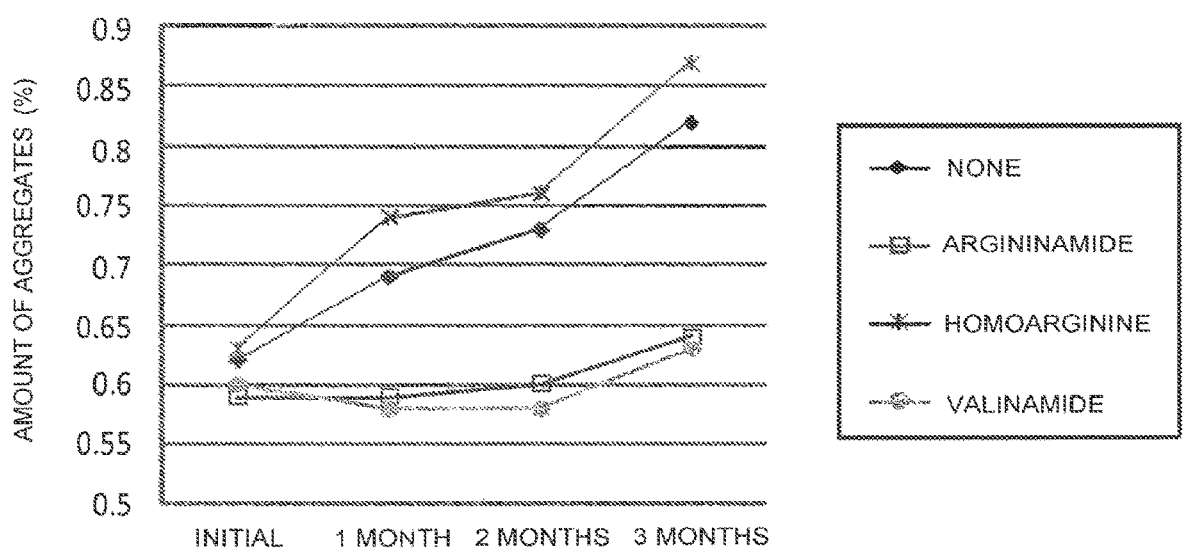
FIG. 5 is a graph showing the changes over time of the amount of aggregates for each of the added compounds when Mab2 was stored at 25° C. for one, two, or three months.
Figure 6:
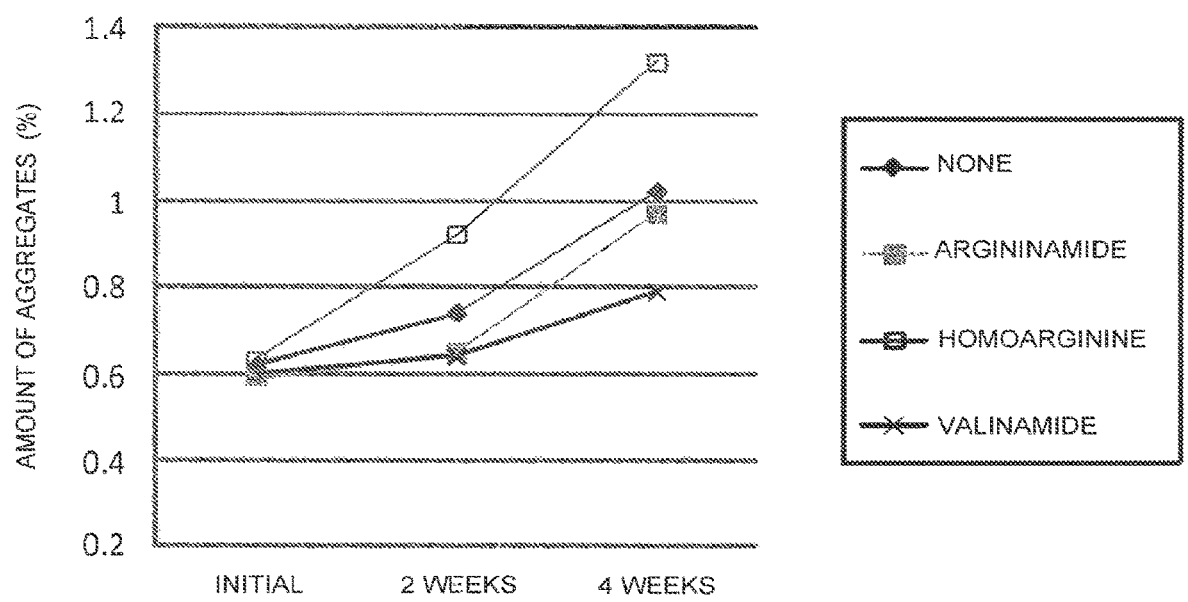
FIG. 6 is a graph showing the changes over time of the amount of aggregates for each of the added compounds when Mab2 was stored at 40° C. for two or four weeks.

Results showing the change over time of the amount of aggregates at 25° C. storage are shown in FIG. 5 and Table 10, and results indicating the change over time of the amount of aggregates at 40° C. storage are shown in FIG. 6 and Table 11. FIGS. 5 and 6 show graphs that exclude the data for arginine ethyl ester. In the thermal acceleration study at 25° C., the result showed hardly any increase or decrease of aggregates by the formulas with valinamide or argininamide added. In the photoirradiation study, the formulas with argininamide or valinamide added showed the lowest amount of aggregate increase as shown in Table 12. Arginine ethyl ester showed the next lowest amount of aggregate increase.

TABLE 10

| ADDITIVE mmol/L | | INITIAL | 1 MONTH | 2 MONTHS | 3 MONTHS |
|---|---|---|---|---|---|
| NONE | 0 | 0.62 | 0.69 | 0.73 | 0.82 |
| ARGININAMIDE | 150 | 0.59 | 0.59 | 0.60 | 0.64 |
| ARGININE ETHYL ESTER | 150 | 0.60 | 1.20 | 1.89 | 3.35 |
| HOMOARGININE | 150 | 0.63 | 0.74 | 0.76 | 0.87 |
| VALINAMIDE | 150 | 0.60 | 0.58 | 0.58 | 0.63 |

TABLE 11

| ADDITIVE mmol/L | | INITIAL | 2 WEEKS | 4 WEEKS |
|---|---|---|---|---|
| NONE | 0 | 0.62 | 0.74 | 1.02 |
| ARGININAMIDE | 150 | 0.59 | 0.65 | 0.97 |
| ARGININE ETHYL ESTER | 150 | 0.60 | 54.50 | N.T. |
| HOMOARGININE | 150 | 0.63 | 0.92 | 1.32 |
| VALINAMIDE | 150 | 0.60 | 0.64 | 0.79 |

TABLE 12

| ADDITIVE mmol/L | | AMOUNT OF AGGREGATE INCREASE (%) |
|---|---|---|
| — | 0 | 2.19 |
| ARGININAMIDE | 150 | 0.21 |
| ARGININE ETHYL ESTER | 150 | 0.27 |
| HOMOARGININE | 150 | 1.04 |
| VALINAMDE | 150 | 0.21 |

[Example 5] Assessment of Stabilization Effects of Additives Using Mab3

Mab3 (tocilizumab) was expressed by a method known to those skilled in the art using a stably expressing CHO cell line, purified to high purity by a method known to those skilled in the art, and then stored in the form of a highly-concentrated Mab3 stock solution (248 mg/mL Mab3, 7.7 mM histidine, pH6.3); and this was used for the stability studies in the Example described below.

Testing Method:

Using Mab3, the stability of the compounds added to the additive-free formula was evaluated by thermal acceleration test and photoirradiation test. Samples were prepared by adding a pre-prepared solution of appropriate composition to a highly-concentrated Mab3 stock solution to adjust the concentrations of each of the components to the concentrations shown in Table 13. Thermal acceleration studies and photoirradiation studies were carried out under conditions similar to those of Example 3. After the respective studies, size exclusion chromatography was performed under conditions similar to those of Example 3, and the respective contents (%) were calculated by the area percentage method.

TABLE 13

| SAMPLE NO. | ANTIBODY mg/mL | HISTIDINE mmol/L | ADDITIVE | mmol/L | PS80 mg/mL | pH |
|---|---|---|---|---|---|---|
| E1 | 180 | 20 | — | 0 | 0.2 | 7.0 |
| E2 | 180 | 20 | ARGININE | 100 | 0.2 | 7.0 |
| E3 | 180 | 20 | ARGININAMIDE | 100 | 0.2 | 7.0 |
| E4 | 180 | 20 | ARGININE ETHYL ESTER | 100 | 0.2 | 7.0 |
| E5 | 180 | 20 | HOMOARGININE | 100 | 0.2 | 7.0 |
| E6 | 180 | 20 | VALINAMIDE | 100 | 0.2 | 7.0 |

In the thermal stability study at 25° C., the amount of aggregate increase from one to three months was significantly low in the formulas containing argininamide, arginine ethyl ester, or valinamide, and was increased most in the additive-free formula. The thermal stability study at 40° C. also showed the lowest amount of aggregate increase from two weeks to four weeks in the formula containing argininamide. Similarly, in the photoirradiation study, while an increase of aggregates was observed for the additive-free formula, changes in aggregates were hardly seen in the samples formulated using argininamide, arginine ethyl ester, or valinamide.

INDUSTRIAL APPLICABILITY

The present invention provides protein-comprising formulations with excellent stability.

In particular, the present invention provides highly-concentrated antibody-comprising formulations with excellent stability against photostress.

Furthermore, the present invention enables provision of highly-concentrated antibody-comprising formulations by suppressing photostress-induced aggregation in formulations in the solution form. The highly-concentrated antibody-comprising formulations of the present invention are stable against photostress, and therefore, they can be stably stored for a long time in the form of a solution. Stability against photostress is advantageous in that there is little concern regarding the light-blocking properties of the container used to store antibody formulations.

The invention claimed is:

1. A method for suppressing protein aggregation caused by photostress, comprising adding valinamide to a protein-containing sample.

2. A method for suppressing protein destabilization caused by photostress, comprising adding valinamide to a protein-containing sample.

3. The method of claim 1, wherein the protein is an antibody.

4. A method for suppressing protein aggregation caused by photostress, comprising adding valinamide to a protein-comprising sample, in combination with a surfactant.

5. A method for suppressing protein destabilization caused by photostress, comprising adding valinamide to a protein-comprising sample, in combination with a surfactant.

6. The method of claim 4, wherein the protein is an antibody.

7. A method for producing a stabilized protein-comprising formulation, which comprises a step of adding valinamide to a protein-comprising sample.

8. The method of claim 5, wherein the protein is an antibody.

9. The method of claim 2, wherein the protein is an antibody.

10. The method of claim 6, wherein the concentrations of valinamide and antibody are 50-150 mM and 1-180 mg/mL, respectively.

11. The method of claim 8, wherein the concentrations of valinamide and antibody are 50-150 mM and 1-180 mg/mL, respectively.

12. The method of claim 9, wherein the concentrations of valinamide and antibody are 50-150 mM and 1-180 mg/mL, respectively.

13. The method of claim 1, wherein the protein-containing sample further comprises histidine buffer comprising arginine.

14. The method of claim 2, wherein the protein-containing sample further comprises histidine buffer containing arginine.

15. The method of claim 4, wherein the protein-containing sample further comprises histidine buffer containing arginine.

16. The method of claim 5, wherein the protein-containing sample further comprises histidine buffer containing arginine.

17. The method of claim 7, wherein the stabilized protein-comprising formulation further comprises histidine buffer containing arginine.

18. The method of claim 10, which further comprises adding 10-30 mM histidine buffer and 10-100 mM arginine to the protein-containing sample.

19. The method of claim 11, which further comprises adding 10-30 mM histidine buffer and 10-100 mM arginine to the protein-containing sample.

20. The method of claim 12, which further comprises adding 10-30 mM histidine buffer and 10-100 mM arginine to the protein-containing sample.

21. A method for producing a stabilized protein-comprising formulation, which comprises a step of adding valinamide to a protein-comprising sample, in combination with a surfactant.

22. The method of claim 21, wherein the protein is an antibody.

23. The method of claim 22, wherein the concentrations of valinamide and antibody are 50-150 mM and 1-180 mg/mL, respectively.

24. The method of claim 23, wherein the stabilized protein-comprising formulation further comprises histidine buffer containing arginine.

* * * * *